United States Patent [19]

Eisenberg et al.

[11] Patent Number: 5,492,117
[45] Date of Patent: Feb. 20, 1996

[54] SYSTEM AND METHOD FOR ASSESSING MEDICAL RISK

[75] Inventors: Alan J. Eisenberg, Monmouth Junction, N.J.; Alexander Adelson, Peekskill, N.Y.

[73] Assignee: Base Ten Systems, Inc., Trenton, N.J.

[21] Appl. No.: 239,811

[22] Filed: May 9, 1994

Related U.S. Application Data

[63] Continuation of Ser. No. 67,305, May 26, 1993.

[51] Int. Cl.⁶ .......................................... A61B 5/00
[52] U.S. Cl. ............................................ 128/630
[58] Field of Search ............................. 128/630, 897, 128/898; 395/924; 364/413.01, 413.02, 413.07–413.09, 413.1, 413.11

[56] References Cited

U.S. PATENT DOCUMENTS

| | | | |
|---|---|---|---|
| 4,864,492 | 9/1989 | Blakely-Fogel et al. | 364/200 |
| 5,258,907 | 11/1993 | Macri | 364/413.01 |
| 5,316,953 | 5/1994 | Macri | 436/87 |
| 5,324,667 | 6/1994 | Macri | 436/518 |

*Primary Examiner*—Angela D. Sykes
*Assistant Examiner*—Samuel Gilbert
*Attorney, Agent, or Firm*—Sprung Horn Kramer & Woods

[57] ABSTRACT

A system and method for assessing the medical risk of a given outcome for a patient comprises obtaining test data from a given patient corresponding to at least one test marker for predicting the medical risk of a given outcome and obtaining at least one variable relating to the given patient and transforming the test data with the variable to produce transformed data for each test markers. A database of transformed data from previously assessed patients is provided and mean and standard deviation values are determined from the database in accordance with the actual occurrence of the given outcome for previously assessed patients. The transformed data is compared with the mean and standard deviation values to assess the likelihood of the given outcome for the given patient and the database is updated with the actual occurrence for the given patient, whereby the determined mean and standard deviation will be adjusted.

10 Claims, 2 Drawing Sheets

SYSTEM AND METHOD FOR ASSESSING MEDICAL RISK

This application is a continuation of application Ser. No. 08/067,305, filed May 26, 1993.

BACKGROUND OF THE INVENTION

The present invention relates to a system and method of assessing the medical risk of a given outcome for a given patient, and, in particular to prenatal risk evaluation.

Maternal serum alpha-fetoprotein (MSAFP) screening for the detection of fetal abnormalities and abnormal pregnancies has been used for over twenty years by obstetricians and geneticists. AFP screening is particularly applicable to women who conceive over the age of 35, a time point at which the incidence of abnormal pregnancies and fetal defects increases dramatically. An elevation in MSAFP is associated with a number of fetal anomalies, including open neural tube defects such as spina bifida and anencephaly, congenital nephrosis, and gastrointestinal tract abnormalities.

In 1984, a low maternal serum AFP level was reported to be predictive of fetal chromosomal anomalies as well, including the risk of Down's Syndrome. Since a low maternal serum AFP value is effective in identifying only 20% of Down's Syndrome affected cases, additional markers were sought which could add to the predictive value of this test. Maternal serum human chorionic gonadotropin (hCG) and unconjugated estriol (uE3) levels have both been described as providing additional information, useful for estimating the probability of fetal Down's Syndrome.

The evidence that hCG measurements provide an additional prognostic marker of Down's Syndrome risk in afflicted pregnancies is considerably stronger than the contribution of unconjugated estriol (uE3). However, many laboratories have incorporated all three tests, AFP, hCG, and uE3, for prenatal screening programs targeted at high risk pregnancy populations.

In the course of attempting to optimize the use of MSAFP testing, a number of variables have been identified which can influence the interpretation of AFP results. Besides developing normative data matched to the gestational period, since AFP appears in the maternal circulation normally with increasing concentration as pregnancy develops, maternal weight, race and diabetic status have also been shown to be confounding variables which can alter the reference base by which one judges the result to be normal or abnormal. This has necessitated the establishment of median values for MSAFP from a normal, healthy pregnancy population between 14 and 20 weeks of gestation (EGA). Also, the normal variability of MSAFP at each week of gestation has been evaluated, and found to span a range of 2.5 multiples of the median (MoM). Once the MoM value from the MSAFP is calculated, the influence of maternal weight, race, and diabetic status on the MoM calculation is determined using correction factors established from the literature. The final adjusted MoM value is interpreted by comparison to the normal database. The clinical interpretation of these markers is dependent on their relationship to each other, as well as the specimen source and EGA.

SUMMARY OF THE INVENTION

The main object of the present invention is to provide an optimal and efficient approach to using the markers to evaluate the combined influence of the numbers (AFP, hCG, and uE3) for a specific EGA and source.

Another object is to provide an interpretative report, integrating all of the test results within the context of the patient's present gestational period, weight, race, and diabetic status, when applicable. Placing the AFP result on a graph, normalized to MoM range and EGA, further facilitates the interpretation of the results.

The present invention allows for simple entry of data into the system so that all of the information needed to provide appropriate adjustments to the MoM value, including the patient's age, weight, race and diabetic status, is accessible. The system allows printing of an interpretative letter that includes, in tabular form, the raw data for each of the markers tested, the adjusted MoM value(s), and the probability statistics for Down's Syndrome based on age alone, and age in combination with all prenatal markers entered. Elevated AFP results are also quantified and presented as an indicator of open neural tube defects. The system is able to formulate customized statements to accompany those results, depending upon the MoM calculations. Also included is a graph which shows where the patient's marker value fell in relationship to a normal pregnancy for that particular week of gestation. The use of both numerical and visual data helps to convey the findings and avoids errors.

Another feature of the present invention is the ability to continuously update the reference database and median scores for each week of gestation as more normal pregnancy results are entered therein.

A further feature of the invention is the ability to enter data relating to the actual outcome and to continue to refine and update the normative database used to calculate the median, means and standard deviation values.

The system uses at least one of three prenatal markers: AFP (alpha feto-protein), hCG (human chorionic gonadotrophin), and uE3 (unconjugated estriol). The source for these tests can be patient's (maternal) serum or amniotic fluid. The measured values of these markers are compared to the median for that marker, source and gestational age. Corrections are applied for maternal weight, race and diabetic status.

A further object of the present invention is to provide validation of the data to achieve a safety critical environment for the system. In accordance with the invention, criteria and requirements are set for all of the data that is both entered by the user and calculated by the system so as to prevent errors in data entry, system software and system hardware.

These and other features and advantages of the present invention are achieved in accordance with the present invention by a system and method for assessing the medical risk of a given outcome for a patient with data input means receptive of test data from a given patient corresponding to at least one test marker for predicting the medical risk of a given outcome and at least one variable relating to the given patient, means for transforming the test data with the variable to produce transformed data for each test marker, means storing a database of transformed data from previously assessed patients, means for determining mean and standard deviation values from the database in accordance with the actual occurrence of the given outcome for previously assessed patients, means for comparing the transformed data with the mean and standard deviation values to assess the likelihood of the given outcome for the given patient, and means for updating the database with the actual occurrence for the given patient, whereby the determined mean and standard deviation will be adjusted.

The system also preferably has means for storing predetermined requirements for risk data comprising the test data, the at least one variable, the transformed data, the determined mean and the determined standard deviation, means for validating the data when received, transformed and determined with regard to the predetermined requirements and means for indicating when the data does not meet the requirements. The validating means preferably includes means for checking the integrity of the database for each comparison with the data therein and each update of the data therein, means for range checking the test markers, the test data and the transformed data for the given patient, means for double copy comparing all data received from and written into the storing means and means for maintaining an archival log of all data changes to the database. When at least two markers are used, the system preferably includes means for correlating the comparisons of the transformed data for the at least two markers. The system and method also include means for storing a plurality of letters, means for selecting a letter based on the transformed data for the given patient and means for printing the selected letter.

The present invention also includes a method of validating data input in a system by a user, comprising the steps of predefining a set of criteria for all data to be input, storing the set of criteria, presenting the criteria to a user when data is input, comparing the inputted data to the stored criteria, and indicating to the user when the data does not adhere to the stored criteria. Preferably, a set of criteria for data to be calculated is predefined, the calculated data is compared to the stored criteria and an indication is made to the user when the calculated data does not adhere to the criteria. The user is preferably permitted to modify the criteria in response to an indication of non-adherence.

In another embodiment of the invention, a system for validating data input by a user, comprises means storing a predefined set of criteria for all data to be input, means for presenting the criteria to a user when data is input, means for comparing the inputted data to the stored criteria, and means for indicating to the user when the data does not adhere to the stored criteria. The system preferably comprises means for storing a set predefined set of criteria for data to be calculated, means for comparing calculated data to the stored criteria and means for indicating to the user when the calculated data does not adhere to the criteria. In a preferred embodiment, the system further comprises means for permitting the user to modify the criteria in response to an indication of nonadherence.

These and other features and objects of the present invention will be apparent from the following detailed description of the invention taken with the attached drawings wherein:

DETAILED DESCRIPTION OF THE INVENTION

Figure 1:
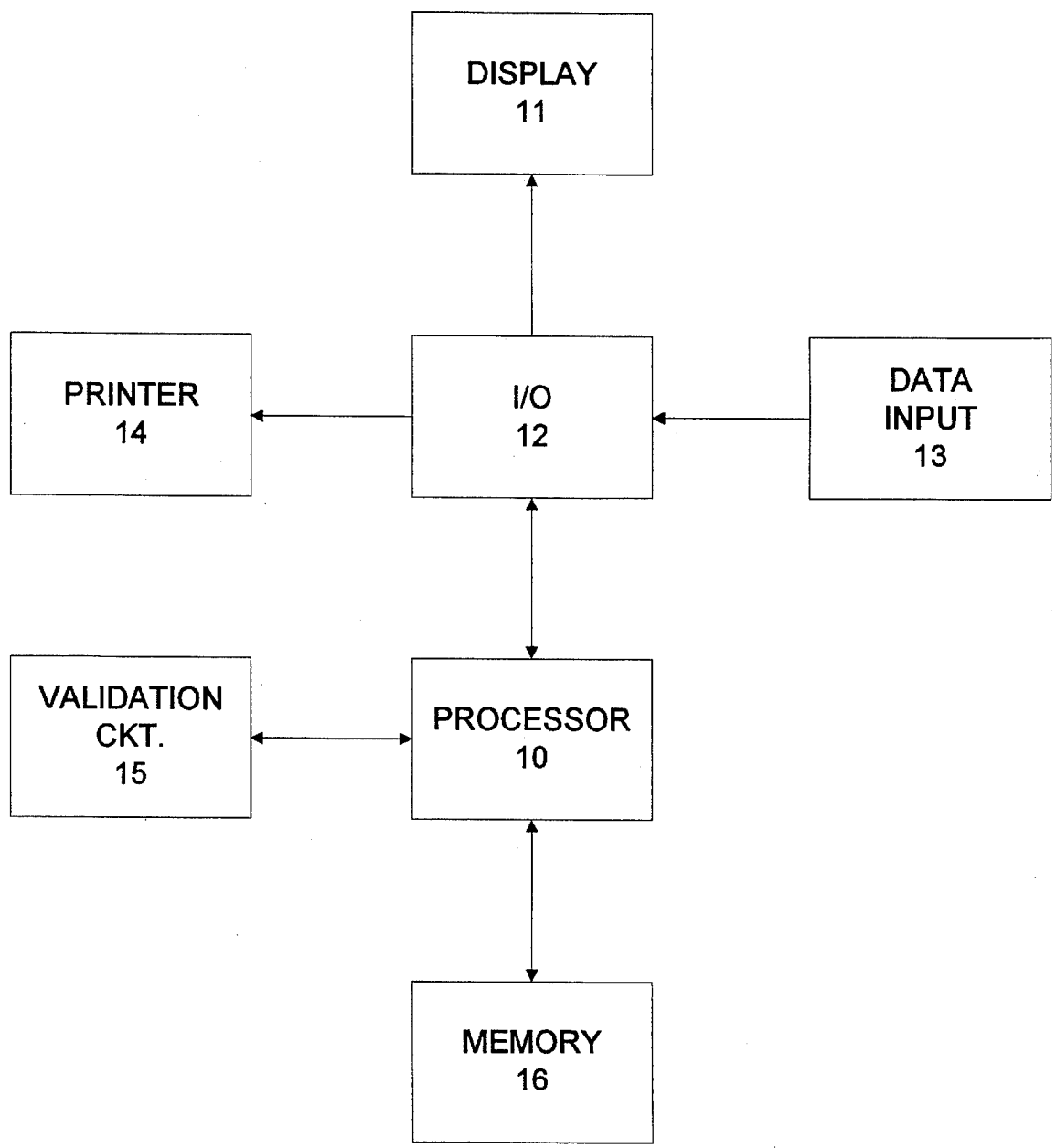
FIG. 1 is a block diagram of the system according to the present invention.

Referring to FIG. 1, the system according to the present invention includes a processor 10 capable of writing data into a memory 16 and reading data from memory 16 as demanded. The processor 10 is also connected to an input/output circuit 12 which accepts data from a data input device including a keyboard, a mouse and/or a floppy disk drive and which outputs data from the processor to a display 11 which includes a monitor and a printer 14 which is preferably a dot matrix, laser or ink jet printer.

In accordance with the invention, elements 10–13 and 16 can be provided by an Apple Macintosh Plus or later computer having two megabytes of RAM, a hard drive including at least 20 megabytes of memory, an operating system comprising system 6.0 or greater and including system 7. The printer can be any printer of the above-mentioned type which is capable of printing both text and graphics.

Another part of the system is validation circuitry 15 which interacts with the processor 10 to provide a safety critical environment for the system. As will be discussed hereinafter, the system and the user set up requirements and criteria for all of the data that is input by the user through data input 13, the data stored in memory 16 as part of the database and the data which is calculated in processor 10 in order to carry out the method of the present invention. Circuitry for effecting the validation circuit 15 is disclosed by way of example in copending U.S. application Ser. No. 07/964,742 filed Oct. 22, 1992 and U.S. application Ser. No. 07/983,489 filed Nov. 30, 1992, the disclosures of which are incorporated herein by reference.

The data stored in memory 16 comprises the database including patient information, the prenatal test results and letters to be used depending upon the test results as will be described hereinafter.

The processor 10 evaluates the marker values input through data input 13, based on the median score for the test, given the test source and the status of the pregnancy. These medians use both historical data and those calculated from the test results stored in the database. The historical medians are included as default values which aid in the validation of data as will be described hereinafter.

Because of the importance of the tests and the ability for errors to either prevent the indication of a risk or to indicate a risk when there is none, a safety critical environment is provided for the system.

Figure 2:
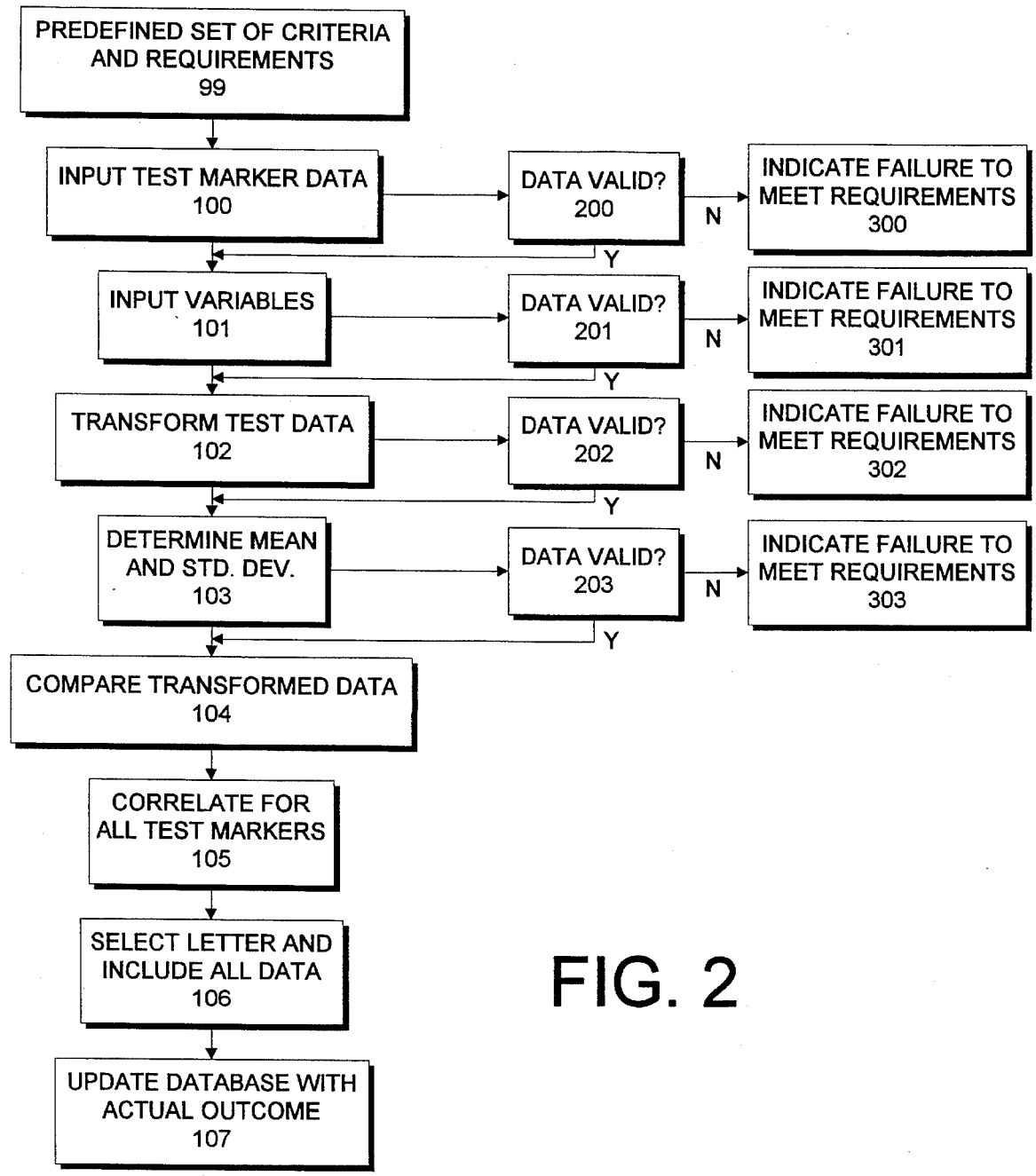
FIG. 2 is a flow chart of the method according to the present invention.

FIG. 2 shows the flow chart for the operation of the system of FIG. 1.

Upon the initial set up of the system, a predefined set of criteria and requirements are loaded into memory in step 99. These criteria and requirements include expected values or range of values for all inputted data and calculated data, for example, a measured low and measured high value is input into memory 16 for each marker used. These represent the expected lowest and highest measurements for that marker and any attempt to enter a value for that marker which is out of the range of these two parameters will result in a warning message being displayed on display 11.

The system also stores a normal MoM low and normal MoM high value for each marker. These values are used to measure the calculated MoM values for each marker to determine whether an error has occurred in the computation of the MoM values due to either a software or hardware failure. When the calculated MoM value is outside this range, the user is warned of a possible error on display 11.

While the flow chart shows the inputting of test marker data in step 100, prior to the input of variables in step 101, it is understood that these steps can be reversed. The data relating to the test marker is input and checked against the range data stored in memory 16 by validation circuit 15. If the input test marker data is outside the expected range for that marker, the display 11 will indicate the failure to meet the requirements in step 100 so that the user must either change the input data or indicate to the system that this unusual data is acceptable, thereby temporarily changing the criteria or requirements of the system.

The same is true for the inputting of variables such as race, weight, age and diabetic status in step 101. If the data is outside the range of valid data stored in memory 16 and checked by validation circuit 15 in step 201, display 11 will indicate the failure to meet requirements in step 301 and ask the user to reevaluate the data input into the system.

Upon accepting the test marker data and input variables, the system then transforms the test data in step 102 so it can be used with the database in memory 16.

Studies have implicated various maternal variables as effecting the interpretation of AFP results. Black and Asian maternal serum AFP levels are approximately 10% higher than caucasian levels at the same EGA. Also the levels of women with IDDM (Insulin Dependent Diabetes Melitis) is about 40% higher than those of non-diabetic control patients. It has also been found that maternal weight effects the interpretation of serum AFP levels and it is therefore desirable to alter the MoM based on the current maternal weight.

Thus in the transforming step 102, the test results are adjusted for diabetes and race, the multiple of median is calculated therefrom and the multiple of median is adjusted for the weight of the mother.

Median scores are used to derive the multiple of median for each individual by taking the ratio between the test result and a median value. Medians are classified by gestational age of the fetus (EGA), the prenatal marker and the source of the test. The median can either be preset by the user for each of the markers or it can be calculated from the values in the database. In any event, the normal MoM low and high fields for each marker which are stored in memory 16 are used by the validation circuit to validate the median used in each calculation in step 202 in order to determine whether and error has occurred in either system software of hardware. If the user sets a median value which is outside the normal range, or if the system calculates a median value which is outside a normal range, the system will indicate the failure to meet the requirements of the system in step 302 and require the user to reprocess the information or indicate that the system should use this data despite its possible error.

After the multiple of median data is calculated for each marker for the given patient, the processor 16 determines the mean and standard deviation of the values stored in the database for all previously assessed patients for each of the markers. These calculated mean and standard deviation values are compared to predetermined outside range values in step 203 by validation circuitry 15 to determine if these calculated values meet the requirements of the system. If they do not, the system indicates the failure to meet requirements in step 303 on display 11 so that the user is informed of the possibility of either a software of hardware failure or that the database itself has become corrupted.

If the mean and standard deviation values computed by the system are valid, the processor 10 compares the transformed test data from step 102 with the mean and standard deviation values for each marker to determine the risk factors for each marker. The system then correlates the risk factors for all of the test markers in step 105 and determines a computed risk for Down's Syndrome and neural tube defects.

A large body of evidence has been accumulated, associating maternal serum (and to a lesser extent, amniotic fluid) AFP levels with some fetal anomalies. A high serum AFP level, above the cited normal limit of 2.5 times the median for that EGA (2.5 MoM), is associated with an increased risk of open neural tube defects (NTD), presumably because the AFP has leaked through the ND into the amniotic fluid, and eventually, into the maternal blood stream. Conversely, a low serum AFP level, below 50% of the median score for that EGA (0.5 MoM), has been associated with fetal Down's Syndrome and, less strongly, to other chromosomal abnormalities, including some of the other trisomies.

Recent work has focused on refining the predictions using AFP, and also evaluating whether hCG or uE3 would make the predictions more sensitive and accurate. The best method of predicting the risk of fetal Down's Syndrome may well include serum AFP, hCG, and uE3, with a reported detection rate of 60-77% or greater. The predictive ability for all three markers for other chromosomal anomalies is not as well defined, nor is the applicability of the tests to non-singleton pregnancies.

The most successful prediction of fetal Down's Syndrome, implements a trivariate Gaussian probability distribution to allow for the influence of all three serum tests (AFP, hCG, uE3) on the well described risk predicted by maternal age alone.

As noted hereinbefore, memory 16 also includes a database of letters regarding the results of the prenatal screening tests. A plurality of letters are present, with each having a prenatal marker range associated with the entered text. One marker is Used as the criterion for choosing which letter to send and the specific value of that marker obtained from the transformed test data in step 102 is used to select the particular type of letter generated by the system. In each case, no matter which letter is selected by the system, each letter includes a listing of all of the input test marker data, all of the input variables, the calculated mean and standard deviation values, the median value used.

The letter also includes graphical data showing the graphs for each of the markers and where the data for each marker for the given patient falls on that graph.

Another important aspect of the present invention is the incorporation of follow-up data in step 107. After the outcome of the pregnancy is known, information on pregnancy outcome is input into the system to test the accuracy of the predictions and to refine the median and mean and standard deviation values which are determined by the system.

Another feature of the data validation circuitry 15 used by the present invention is the maintaining of an activity and transaction log for the system. Aside from the data kept in the database of memory 16, validation circuit 15 maintains a listing of all data input into the system each day including information relating to the specific user who input data.

The validation circuitry 15 also provides a quick check on the system database. It scans all of the files and important file relationships in the database in memory 16 to make sure that the data is intact. Specifically, the circuitry checks the database to see if the data meets the requirements and criteria for the data for each test marker and inputted variable. Validating includes checking the integrity of the database for each comparison with the data therein and each update of the data therein, range checking the test markers, the test data and the transformed data for the given patient, double copy comparing all data received from the database and written therein and maintaining an archival log of all data changes to the database.

The processor 10 also has the ability to permit the exchange of data between one system and another through the I/O 12. The data exchange is implemented by a merge and extract function where data can be extracted from one database and placed on a storage median such as a floppy disk and input via data input 13 to the system. The receiving database then merges the extracted data from the storage median into memory 16.

Data that can be merged and extracted includes patient data and median data. Patient data is extracted by selecting individual patients in the existing database and copying their data to an extraction file. Median data differs from the patient data in that only contains enough information to calculate a set of medians.

It will be appreciated that the instant specification and claims as set forth by way of example and illustration and not limitation and that various modifications and changes may be made without departing from the spirit and scope of the present invention.

What is claimed is:

1. A system for assessing a medical risk of a given outcome for a patient, the system comprising:

data input means receptive of test data from a given patient corresponding to at least one test marker for predicting the medical risk of a given outcome and at least one variable relating to the given patient;

means for transforming the test data with the variable to produce transformed data for each test marker;

means storing a database of transformed data from other medical risk assessment systems for previously assessed patients;

means for determining mean and standard deviation values from the database in accordance with an actual occurrence of the given outcome for previously assessed patients;

means for comparing the transformed data with the mean and standard deviation values to assess a likelihood of the given outcome for the given patient; and means for locally updating the database of said system with the actual occurrence for the given patient;

wherein the means for determining mean and standard deviation values includes means for locally adjusting determined mean and standard deviation values of said system for the locally updated database, whereby adjusted mean and standard deviation values for said system are adjusted for a particular patient population assessed by said system relative to mean and standard deviation values determined from the database from other medical risk assessment systems.

2. The system according to claim 1, further comprising means for storing predetermined requirements for risk data comprising the test data, the at least one variable, the transformed data, the determined mean and determined deviation, means for validating the data when received, transformed and determined with regard to the predetermined requirements and means for indicating when the data does not meet the requirements.

3. The system according to claim 1, for use in assessing prenatal risks, wherein said at least one test marker is selected from the group consisting of AFP, hCG and uE3.

4. The system according to claim 3, wherein said at least one variable is selected from the group consisting of age, race, weight and diabetic status.

5. The system according to claim 1, wherein at least two markers are used and further comprising means for correlating the comparisons of the transformed data for the at least two markers.

6. A method for assessing a medical risk of a given outcome for a patient, comprising the steps of:

obtaining test data from a given patient from a particular patient population corresponding to at least one test marker for predicting the medical risk of a given outcome;

obtaining at least one variable relating to the given patient and transforming the test data with the variable to produce transformed data for each test marker;

providing a database of transformed data from previously assessed patients from other patient populations;

determining mean and standard deviation values from the database in accordance with an actual occurrence of the given outcome for previously assessed patients;

comparing the transformed data with the mean and standard deviation values to assess a likelihood of the given outcome for the given patient; and locally updating the database with the actual occurrence for the given patient and locally adjusting the mean and standard deviation values, whereby adjusted mean and standard deviation values are adjusted for the particular patient population relative to said mean and standard deviation values determined from the database from other patient populations.

7. The method according to claim 6, further comprising providing predetermined requirements for risk data comprising the test data, the at least one variable, the transformed data, the mean and the standard deviation, validating the data when received, transformed and determined with regard to the predetermined requirements and indicating when the data does not meet the requirements.

8. The method according to claim 6, for use in assessing prenatal risk, further comprising obtaining test markers including at least one selected from the group consisting of AFP, hCG and uE3.

9. The method according to claim 8, wherein the step of obtaining variables comprises obtaining at least one variable selected from the group consisting of age, race, weight and diabetic status.

10. The method according to claim 1, wherein at least two markers are used and further comprising correlating the comparisons of the transformed data for the at least two markers.

* * * * *